US010168259B2

(12) United States Patent
Zhang et al.

(10) Patent No.: US 10,168,259 B2
(45) Date of Patent: Jan. 1, 2019

(54) MICROFLUIDIC DEVICES, SYSTEMS, AND METHODS FOR IMAGING TISSUE SAMPLES

(71) Applicant: UNIVERSITY OF NOTRE DAME, Notre Dame, IN (US)

(72) Inventors: Siyuan Zhang, Granger, IN (US); Jeremiah Zartman, Granger, IN (US); David Hoelzle, South Bend, IN (US); Wendy Alvarez Barrios, South Bend, IN (US); Victoria Zellmer, South Bend, IN (US); Cody Narciso, Mishawaka, IN (US)

(73) Assignee: University of Notre Dame, Notre Dame, IN (US)

( * ) Notice: Subject to any disclaimer, the term of this patent is extended or adjusted under 35 U.S.C. 154(b) by 210 days.

(21) Appl. No.: 14/737,986

(22) Filed: Jun. 12, 2015

(65) Prior Publication Data

US 2015/0362411 A1    Dec. 17, 2015

Related U.S. Application Data

(60) Provisional application No. 62/011,158, filed on Jun. 12, 2014, provisional application No. 62/138,043, filed on Mar. 25, 2015.

(51) Int. Cl.
*G01N 1/31* (2006.01)
*B01L 3/00* (2006.01)
(Continued)

(52) U.S. Cl.
CPC ............ *G01N 1/312* (2013.01); *B01L 3/5027* (2013.01); *G02B 21/34* (2013.01); *B01L 3/54* (2013.01);
(Continued)

(58) Field of Classification Search
CPC .............................. G01N 1/312; B01L 3/5027
(Continued)

(56) References Cited

U.S. PATENT DOCUMENTS 6,632,619 B1 * 10/2003 Harrison .............. B01J 19/0093
422/504
8,372,657 B2    2/2013 Rebound et al.
(Continued)

FOREIGN PATENT DOCUMENTS

WO    2014043635 A1    3/2014

OTHER PUBLICATIONS

Passeraub et al., Design, microfabrication and analysis of a microfludic chamber for the perfusion of brain tissue slices, 2003, Biomedical Microdevices, 5:2, pp. 147-155.*
(Continued)

*Primary Examiner* — Kevin Joyner
*Assistant Examiner* — Holly M Mull
(74) *Attorney, Agent, or Firm* — Tarolli, Sundheim, Covell & Tummino LLP

(57) ABSTRACT

One aspect of the present disclosure can include a microfluidic device for imaging a tissue sample. The device can include a tissue chamber, a liquid inlet channel, and a liquid outlet channel. The tissue chamber can be defined by a plurality of walls, at least one of which is transparent. The liquid inlet channel can be fluid communication with the tissue chamber. The liquid outlet channel can be in fluid communication with the tissue chamber. The tissue chamber can be sized and dimensioned to completely immobilize the tissue sample during imaging.

19 Claims, 11 Drawing Sheets

(51) Int. Cl.
*G02B 21/34* (2006.01)
*G01N 1/28* (2006.01)

(52) U.S. Cl.
CPC ............... *B01L 2300/0645* (2013.01); *B01L 2300/0654* (2013.01); *B01L 2400/0421* (2013.01); *B01L 2400/0439* (2013.01); *B01L 2400/0487* (2013.01)

(58) Field of Classification Search
USPC ..................................................... 435/288.7
See application file for complete search history.

(56) References Cited

U.S. PATENT DOCUMENTS

| | | | | |
|---|---|---|---|---|
| 2009/0200168 | A1* | 8/2009 | Falk-Jordan | B01L 3/502715 204/601 |
| 2009/0253163 | A1* | 10/2009 | Xie | G01N 1/312 435/40.5 |
| 2010/0003666 | A1 | 1/2010 | Lee et al. | |
| 2010/0196908 | A1* | 8/2010 | Opalsky | B01L 7/52 435/6.1 |
| 2011/0020459 | A1* | 1/2011 | Achrol | B01L 3/502753 424/520 |
| 2013/0143230 | A1 | 6/2013 | Tolias et al. | |
| 2013/0164775 | A1* | 6/2013 | Lausch | G01N 27/327 435/29 |
| 2013/0264205 | A1* | 10/2013 | Hwang | G01N 27/44791 204/451 |
| 2014/0166133 | A1* | 6/2014 | Fu | B01L 3/502738 137/565.01 |

OTHER PUBLICATIONS

Queval et al., Chamber and microfluidic probe for microscopic perfusion of organotypic brain slices, 2010, Lab Chip, 10, pp. 326-334.*
Perrault et al., Integrated microfluidic probe station, 2010, Review of Scientific Instruments, 81, 115107.*
Cheung, Lily S., and Stanislav Shvartsman. "A Multiplex Fluorescent In Situ Hybridization Protocol for Clonal Analysis of *Drosophila oogenesis*." Tissue Morphogenesis. Springer New York, 2015. 115-122.
Chung, Kwanghun, and Karl Deisseroth. "CLARITY for mapping the nervous system." Nature methods 10.6 (2013): 508-513.
Frampton, John P., et al. "Aqueous two-phase system-mediated antibody micropatterning enables multiplexed immunostaining of cell monolayers and tissues." Biotechnology journal 10.1 (2015): 121-125.
Gerdes, Michael J., et al. "Highly multiplexed single-cell analysis of formalin-fixed, paraffin-embedded cancer tissue." Proceedings of the National Academy of Sciences 110.29 (2013): 11982-11987.
Issadore, David, et al. "Microwave dielectric heating of drops in microfluidic devices." Lab on a Chip 9.12 (2009): 1701-1706.
Ke, Meng-Tsen, Satoshi Fujimoto, and Takeshi Imai. "SeeDB: a simple and morphology-preserving optical clearing agent for neuronal circuit reconstruction." Nature neuroscience 16.8 (2013): 1154-1161.
Kumada, Tokimasa, et al. "Improved 1-h rapid immunostaining method using intermittent microwave irradiation: practicability based on 5 years application in Toyama Medical and Pharmaceutical University Hospital." Modern pathology 17.9 (2004): 1141-1149.
Renier, Nicolas, et al. "iDISCO: a simple, rapid method to immunolabel large tissue samples for volume imaging." Cell 159.4 (2014): 896-910.
Shieh, Peyton, et al. "CalFluors: A Universal Motif for Fluorogenic Azide Probes Across the Visible Spectrum." Journal of the American Chemical Society (2015).
Stott, Shannon L., et al. "Isolation of circulating tumor cells using a microvortex-generating herringbone-chip." Proceedings of the National Academy of Sciences 107.43 (2010): 18392-18397.
Tainaka, Kazuki, et al. "Whole-body imaging with single-cell resolution by tissue decolorization." Cell 159.4 (2014): 911-924.
Vlieg, R. C., C. Gillespie, and WM Steve Lee. "Evaluation different passive optical clearing protocols for two-photon deep tissue imaging in adult intact visceral and neuronal organs." bioRxiv (2015): 018622.
Yazdi, Shahrzad, and Arezoo M. Ardekani. "Bacterial aggregation and biofilm formation in a vortical flow." Biomicrofluidics 6.4 (2012): 044114.
Bakhtina, Natalia A., and Jan G. Korvink. "Microfluidic laboratories for C. elegans enhance fundamental studies in biology." RSC Advances 4.9 (2014): 4691-4709.
Mondal, Sudip, et al. "Imaging in vivo neuronal transport in genetic model organisms using microfluidic devices." Traffic 12.4 (2011): 372-385.
Sivagnanam, Venkataragavalu, and Martin AM Gijs. "Exploring living multicellular organisms, organs, and tissues using microfluidic systems." Chemical reviews 113.5 (2013): 3214-3247.
Zeng, Fei, Christopher B. Rohde, and Mehmet Fatih Yanik. "Subcellular precision on-chip small-animal immobilization, multiphoton imaging and femtosecond-laser manipulation." Lab on a Chip 8.5 (2008): 653-656.
PCT International Search Report and Written Opinion for PCT/US2015/035519, dated Sep. 22, 2015, pp. 1-13.

* cited by examiner

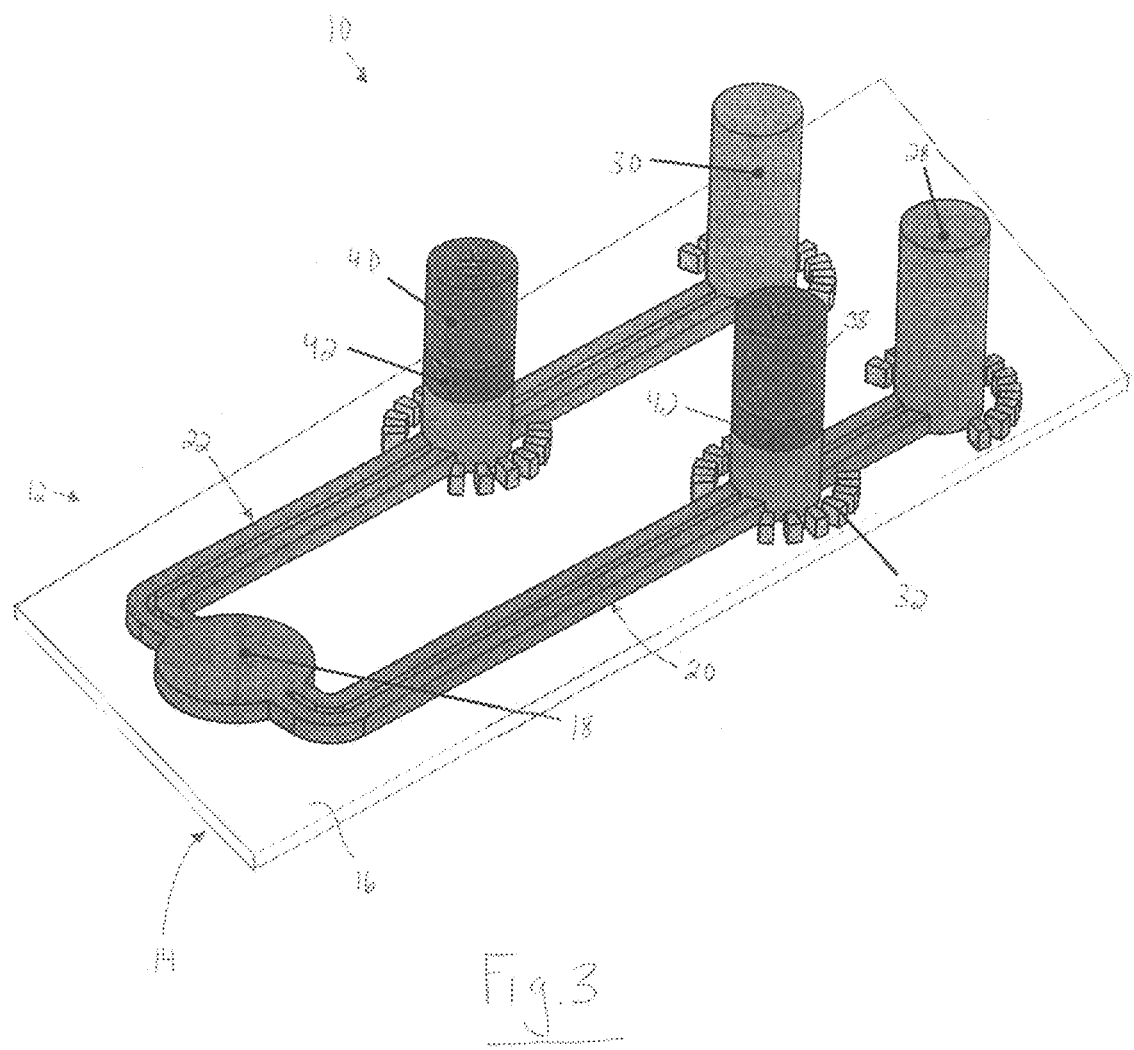

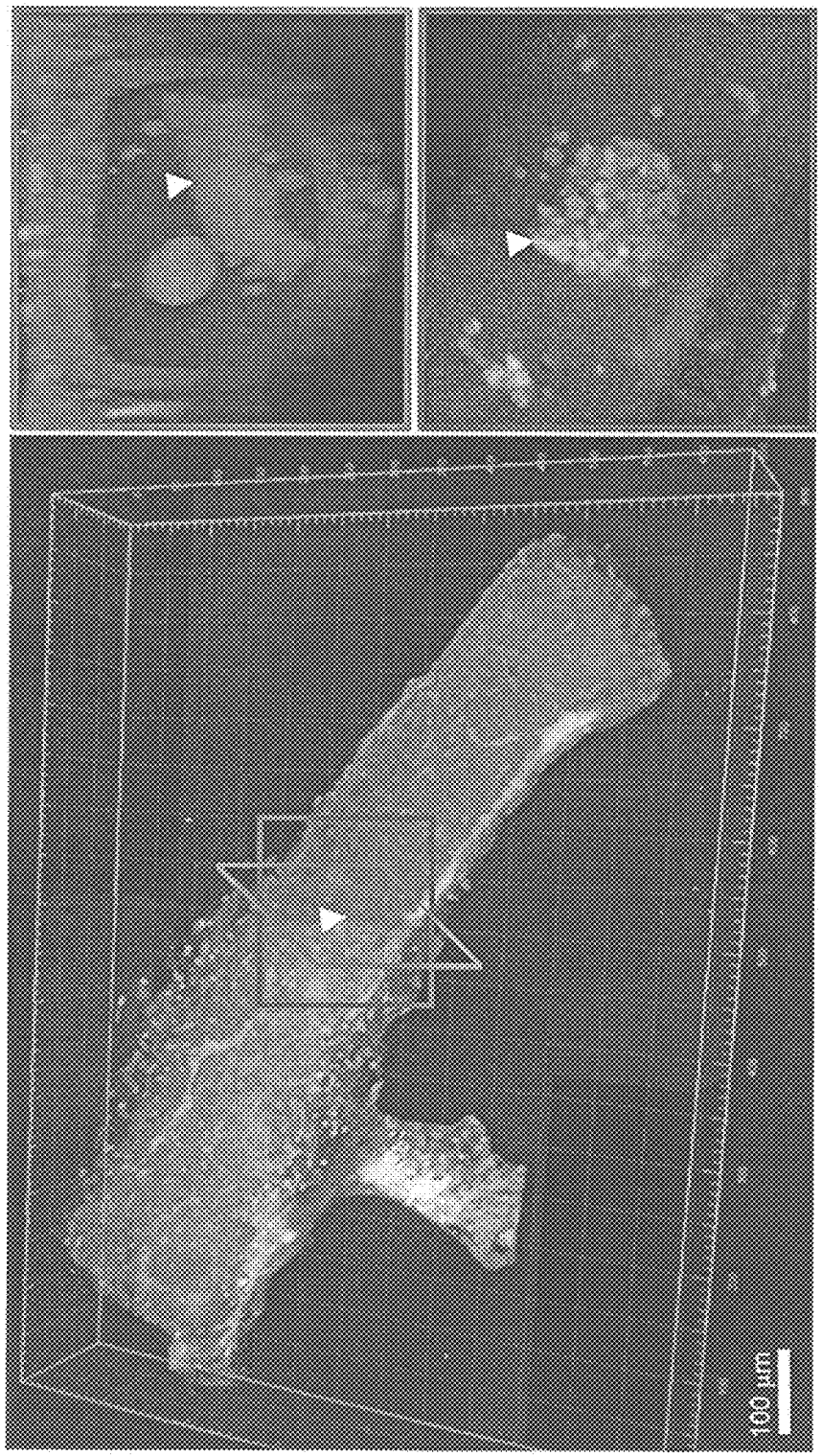
Fig. 9

MICROFLUIDIC DEVICES, SYSTEMS, AND METHODS FOR IMAGING TISSUE SAMPLES

RELATED APPLICATIONS

This application claims the benefit of U.S. Provisional Patent Application Ser. Nos. 62/011,158, filed Jun. 12, 2014, and 62/138,043, filed Mar. 25, 2015, the entirety of each of which is hereby incorporated by reference for all purposes.

TECHNICAL FIELD

The present disclosure relates generally to microfluidic devices and, more particularly, to microfluidic devices, systems, and methods for imaging tissue samples.

BACKGROUND

Microfluidic devices have significantly enhanced the speed, accuracy, and depth of research and development over the course of the past two decades. These devices are typically used to perform sophisticated chemical and biological analyses. One distinct advantage that such lab-on-a-chip technology has provided is the ability to work with very small samples, including molecules and cells.

A microfluidic device has a network of chambers connected by channels; although, some devices simply comprise channels. The channels have microscale dimensions and small quantities of specific liquids can be flowed through these channels. Microfluidic devices may be made at relatively low cost and the channels can be fabricated to perform different types of analytical processes, such as electrophoresis and pressure gradient flow by applying voltage, current, or electrical power to the flow liquid. For example, DNA may be analyzed through the use of a microfluidic device; the microfluidic channels in the specified device may be made compatible with electrophoresis techniques.

The capabilities of existing diagnostic techniques have been improved using microfluidic devices and methods. While these improvements have addressed specific biological issues, such as keeping cells alive ex vivo, these existing systems generally relate to analyzing cellular or molecular compounds instead of larger tissue samples. Additionally, these systems do not address stabilizing a tissue sample in one place throughout performance of multiple processes within the same microfluidic device.

SUMMARY

The present disclosure relates generally to microfluidic devices and, more particularly, to microfluidic devices, systems, and methods for imaging tissue samples.

One aspect of the present disclosure relates to a microfluidic device for imaging a tissue sample. The device can include a tissue chamber, a liquid inlet channel, and a liquid outlet channel. The tissue chamber can be defined by a plurality of walls, at least one of which is transparent. The liquid inlet channel can be fluid communication with the tissue chamber. The liquid outlet channel can be in fluid communication with the tissue chamber. The tissue chamber can be sized and dimensioned to completely immobilize the tissue sample during imaging.

Another aspect of the present disclosure relates to a system for imaging a tissue sample. The system can comprise one or more microfluidic devices, a liquid source, a central acquisition and control module, and an imaging modality. Each of the microfluidic devices can comprise a tissue chamber, a liquid inlet channel, and a liquid outlet channel. The tissue chamber can be defined by a plurality of walls, at least one of which is transparent. The tissue chamber can be sized and dimensioned to completely immobilize the tissue sample during imaging thereof. The liquid inlet channel and the liquid outlet channel can each be in fluid communication with the tissue chamber. The microfluidic device can be immobilized on a translational microscopy stage. The liquid source can be in fluid communication with the liquid inlet channel. The central acquisition and control module can be in electrical communication with the liquid source and the translational microscopy stage. The imaging modality can be in electrical communication with the central acquisition and control module.

Another aspect of the present disclosure can relate to a method for imaging a tissue sample. One step of the method can include providing a system including one or more microfluidic devices having a tissue chamber, a liquid source, a central acquisition and control module, and an imaging modality. A previously withdrawn tissue sample can be placed in the tissue chamber so that the tissue sample is immobilized therein. Next, a liquid that contains at least one labeling agent can be flowed through the tissue chamber whereafter image data of the tissue sample can be obtained. A three-dimensional image of the tissue sample based on the obtained image data can then be obtained.

BRIEF DESCRIPTION OF THE DRAWINGS

The foregoing and other features of the present disclosure will become apparent to those skilled in the art to which the present disclosure relates upon reading the following description with reference to the accompanying drawings, in which:

FIG. 3 is a perspective view of a microfluidic device for imaging a tissue sample constructed in accordance with another aspect of the present disclosure;

FIG. 9 is a 2-photon microscope three-dimensional image of mouse mammary duct section (25×10) stained in accordance with one aspect of the present disclosure (tumor cells inside lumen=blue DAPI; green=F-actin (Phalloidin Alexa fluor 555); and red=anti-cytokeratin 8 (conjugated to Zenon Alexa Fluor 647 rabbit IgG)).

DETAILED DESCRIPTION

Definitions

Figure 1A:
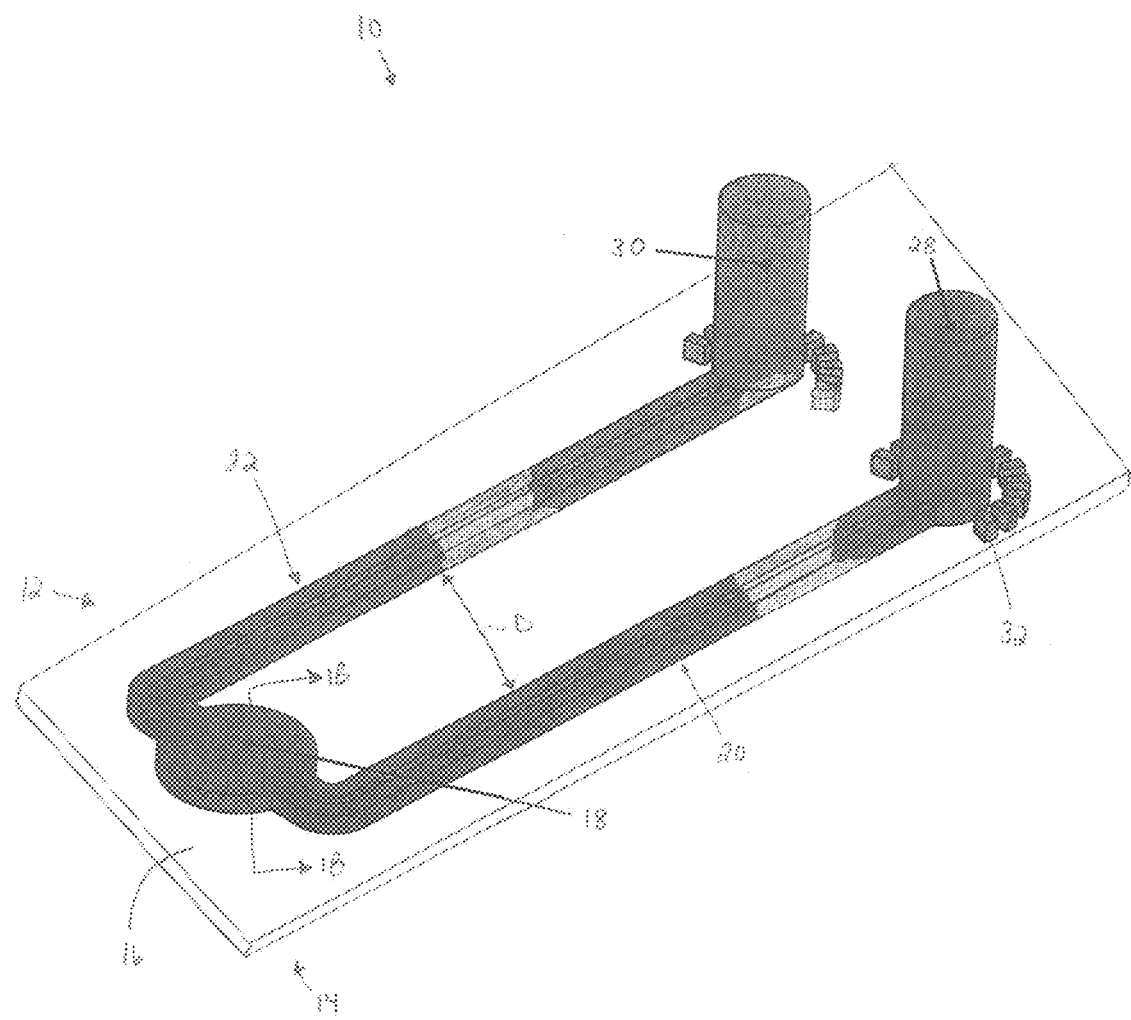
FIG. 1A is a perspective view of a microfluidic device for imaging a tissue sample constructed in accordance with one aspect of the present disclosure.

Unless defined otherwise, all technical and scientific terms used herein have the same meaning as is commonly understood by one of skill in the art to which the present disclosure pertains.

In the context of the present disclosure, the term "subject" can be used interchangeably with the term "patient" and refer to any organism including, but not limited to, human beings, pigs, rats, mice, dogs, goats, sheep, horses, monkeys, apes, farm animals, livestock, rabbits, cattle, insects (e.g., *Drosophila*), fish (e.g., zebrafish), etc.

As used herein, the term "tissue sample" can refer to intact, unprocessed biological tissues as well as tissues that have been processed (e.g., paraffinized or fixed). A tissue sample can be fixed using chemical agents (e.g., formaldehyde, formalin) or other means, such as microwaving, heat treatment, etc. A tissue sample can include an aggregate of cells, whether they are a part of a tissue or a part of an organ. The cells in a particular tissue sample can include the same or several different cell types. In some instances, a tissue sample can be obtained or derived from any portion of a subject by a surgical method. For example, a whole or partial biopsy can be surgically obtained from a subject (e.g., via a core needle biopsy, a fine needle aspiration biopsy, or a surgical or open biopsy). In one example, a tissue sample can be a fresh tissue sample, a freshly-frozen tissue sample, or a preserved tissue sample. In another example, a tissue sample can have a size of at least 10 microns up to about 10 cm or greater.

As used herein, the term "in electrical communication" can refer to a first item or component that is directly or indirectly coupled to a second item or component by at least one conducting medium (e.g., a wire).

As used herein, the term "labeling agent" can refer to any compound, moiety, or agent capable of being detected by an imaging modality. A labeling agent can be chromogenic, fluorescent or chemiluminescent. Non-limiting examples of labeling agents can include tagged small molecules, fluorophore-conjugated antibodies, fluorescent small molecule dyes, fluorescent in situ-hybridized antisense RNA (see, for example, Cheung L S et al., *Methods Mol Biol.* 2015; 1189:115-22), fluorogenic azide probes (see, for example, Shieh, P. et al., *J Am Chem Society* 137(22):7145-7151 (2015), and labeled metabolites bound to tissue through the fixation process.

As used herein, the term "in fluid communication" can refer to a communication between two sections, components, or features of the microfluidic devices and systems of the present disclosure. In some instances, this communication may be a direct connection or a direct path between two sections, components, or features or, alternatively, may include one or more intervening sections in the path between two sections, components, or features of the microfluidic devices and systems of the present disclosure.

As used herein, the term "port" can refer to an opening, recess, or a cavity for providing a pathway for the passage of a liquid or a fluid.

As used herein, the term "multiplexed protein staining" can refer to a method of labeling proteins, mRNA molecules, or other molecules contained within a tissue or associated with a tissue in which more than one label is applied, either sequentially or simultaneously. Standard methods permit 3-4 labels, which by definition is multiplexed staining. A process in which 3-4 labels are applied, imaged, quenched, and then 3-4 new labels are applied, enables a higher dimension of multiplexing and thus more detailed spatial information.

As used herein, the singular forms "a", "an", and "the" can include the plural forms as well, unless the context clearly indicates otherwise. It will be further understood that the terms "comprises" and/or "comprising," as used herein, can specify the presence of stated features, steps, operations, elements, and/or components, but do not preclude the presence or addition of one or more other features, steps, operations, elements, components, and/or groups thereof.

As used herein, the term "and/or" can include any and all combinations of one or more of the associated listed items.

As used herein, phrases such as "between X and Y" and "between about X and Y" can be interpreted to include X and Y.

As used herein, phrases such as "between about X and Y" can mean "between about X and about Y."

As used herein, phrases such as "from about X to Y" can mean "from about X to about Y."

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "directly adjacent" another feature may have portions that overlap or underlie the adjacent feature, whereas a structure or feature that is disposed "adjacent" another feature may not have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms can encompass different orientations of a device in use or operation, in addition to the orientation depicted in the figures. For example, if a device in the figures is inverted, elements described as "under" or "beneath" other elements or features would then be oriented "over" the other elements or features.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or steps) is not limited to the order presented in the claims or figures unless specifically indicated otherwise.

Overview

The present disclosure relates generally to microfluidic devices and, more particularly, to microfluidic devices, systems, and methods for imaging tissue samples. There are at least two overarching challenges in studying molecular events in an intact three-dimensional (3D) tissue context. First, current tissue staining protocols only enable researchers to label up to three proteins of interest by, for example, using three different fluorophore-labeled antibodies and imaging with multi-photon deep tissue imaging or other techniques, such as standard two-dimensional fluorescence, 3D confocal, or light sheet imaging. The number of labeled channels, however, is limited by the overlap in the emission spectrum of the fluorescent markers; approximately 3-4 distinct fluorescent markers can be utilized. And second, with current protocols, it is extremely difficult to co-register multiplexed protein staining from serial rounds of in situ tissue staining experiments within the same tissue sample even with the assistance of sophisticated computer algorithms.

As discussed in more detail below, the present disclosure advantageously provides microfluidic devices, systems, and methods for processing 3D tissue samples that: (1) are faster than current methods by providing a platform such that washings and labeling occur across a small length scale; and (2) secure tissue samples in place such that multiple, sequential labels can be applied to a single tissue sample and then co-registered to greatly enhance the data richness for a sample by enabling multiple immunostains and reconstruction of the full tissue architecture in situ. The present disclosure therefore provides an ideal tissue staining and imaging platform that is integrated and permits immobilization of tissue samples throughout repetitive mounting, clearing, labeling, imaging, de-staining, and re-labeling steps.

The microfluidic devices, systems, and methods of the present disclosure can find application in a variety of medical, biological, and biomedical research fields for diagnostic and/or prognostic purposes. One such field includes cancer biology and, in particular, the progression of cancer in the context of the tumor microenvironment (TME). The translation of knowledge about the TME to the clinic is intrinsically challenging owing to the unique nature of tumor-TME interactions—a dynamic process with unique spatial and temporal characteristics. Traditional clinical diagnostic assays (e.g., immunohistochemistry or IHC), which are based on thin (~5-10 µm) tissue sections cannot faithfully interrogate whole tissue biopsy cytotypes (i.e., the cellular identity, quantity, and location of various cell types that comprise a tumor and its 3D microenvironment). Advantageously, the present disclosure provides a robust platform that can systematically integrate genetic and morphological information from patient biopsies and provide more comprehensive and accurate diagnoses of early stage cancer and to predict tumor prognosis.

The present disclosure can also find application in the field of histology, where protein quantification is routinely performed. Traditional histology methods only enable two-dimensional protein quantification. The microfluidic devices, systems, and methods of the present disclosure advantageously have the ability to bring in situ 3D protein quantification to the study of whole tissue structures and cell-tissue interaction(s).

Further applications and advantages of the present disclosure are discussed below.

Microfluidic Devices

One aspect of the present disclosure can include a microfluidic device 10 (FIGS. 1A-B) for imaging a tissue sample. The microfluidic device 10 can have a two-layer configuration comprising a feature side 12 that is coupled to a transparent (or substantially transparent) substrate 14. As described in detail below, the feature side 12 can include various structural components and features of the microfluidic device 10. All or only a portion of the structural components and features can be formed from one or combination of materials, such as a polymeric organosilicon compound (e.g., polymethylsiloxane or PDMS), polystyrene, glass, quartz, and the like. The substrate 14 can be optically clear and capable of transmitting light therethrough. In one example, the substrate 14 can be formed from glass (e.g., a coverslip). The structural components and features that form the feature side 12 of the microfluidic device 10 can be coupled to a first major surface 16 of the substrate 14 using one or a combination of attachment techniques, such as suction, chemical bonding, clamps, and the like.

Various manufacturing methods can be used to form the microfluidic device 10, as will be appreciated by those in the art. Exemplary methods include, but are not limited to, a variety of micromachining and microfabrication techniques, including film deposition processes such as spin coating, chemical vapor deposition, laser fabrication, photolithographic and other etching techniques using either wet chemical processes or plasma processes, embossing, injection molding and bonding techniques. In addition, there are printing techniques for the creation of desired fluid guiding pathways; that is, patterns of printed material can permit directional fluid transport. In one example, soft lithography can be used to form all or only a portion of a microfluidic device 10.

In one example, a microfluidic device 10 can comprise a tissue chamber 18, a liquid inlet channel 20 in fluid communication with the tissue chamber, and a liquid outlet channel 22 in fluid communication with the tissue chamber. The tissue chamber 18 can be defined by a plurality of walls 24, at least one of which is transparent. As shown in FIG. 1B, the transparent wall 26 defining a portion of the tissue chamber 18 can comprise a portion of the substrate 14 (e.g., a portion of the first major surface 16). The remainder of the tissue chamber 18 can be defined by the walls 24 associated with the feature side 12 of the microfluidic device 10. In some instances, one or more interior surfaces defining the tissue chamber 18 can include a groove (not shown) or grooves to permit liquid flow around the tissue sample. Although the tissue chamber 18 is depicted as having a disc-shaped configuration in FIG. 1A, it will be appreciated that other shapes are possible (e.g., square, rectangular, cylindrical). In one example, the tissue chamber 18 can have a disc-shaped configuration with a diameter of between about 1-4 mm (e.g., 1.4 mm). In another example, the tissue chamber 18 can have a cylindrical and rotatable configuration to enable 360-degree viewing of the tissue sample.

The tissue chamber 18 can be sized and dimensioned to completely immobilize a tissue sample during imaging. The fact that tissue samples are immobilized in the tissue chamber 18 is advantageous because securing tissue samples in a single place ensures that clearing solutions, immunostains, and washing buffers can be flowed through the tissue chamber while the tissue sample maintains its orientation. For example, because the tissue chamber 18 holds a tissue sample in place, positions in a particular tissue sample can be tagged and recalled—in the same orientation—after rinsing and re-staining with different labeling agents. The configuration of the tissue chamber 18 thus allows the application of multiple, sequential labels to a single tissue sample, which can then be co-registered to greatly enhance the data richness by enabling multiple immunostains and reconstruction of the full tissue architecture using digital image processing. This is unlike conventional imaging platforms, which require that tissue samples be manipulated throughout repetitive mounting, clearing, labeling, imaging, de-staining, and re-labeling steps. Also, the fact that tissue samples are immobilized in the tissue chamber 18 advantageously allows direct imaging of tissue samples with subsequent co-registration of multiple imaging datasets without disassembling the microfluidic device 10.

It will be appreciated that the tissue chamber 18 can include other features or components not illustrated in FIGS. 1A-9. For example, the tissue chamber 18 can include a hydro-mold material (e.g., a porous calcium alginate hydrogel) can be disposed in the tissue chamber 18 and configured to partially or completely envelop the tissue sample, which advantageously allows for liquid flow through the tissue chamber without changing the orientation of the tissue sample. Additionally or optionally, the tissue chamber 18 can include a removable plug that permits access to its interior for loading and removal of a tissue sample therefrom.

The portion of the substrate 14 that forms the tissue chamber 18 can include an embedded or etched marker (or markers) (not shown) to facilitate orientation of the microfluidic device 10. Non-limiting examples of such markers can include an embedded fluorescent scale bar to facilitate repetitive measurements, a QR code, or any other identification system capable of labeling individual samples and/or tissue chambers 18.

Figure 1B:
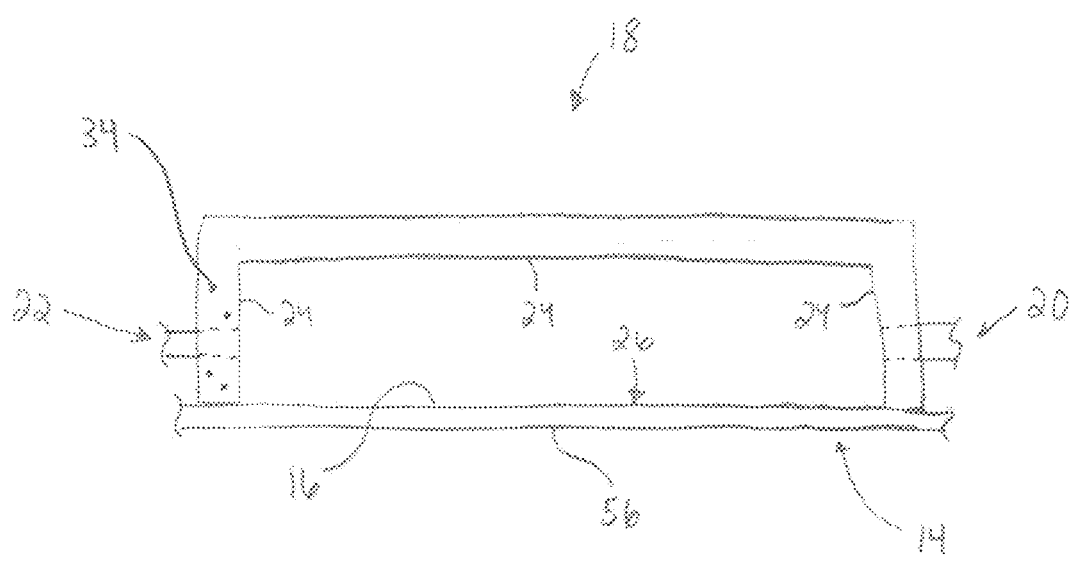
FIG. 1B is a cross-sectional view taken across Line 1B-1B in FIG. 1A.

Referring to FIG. 1A, two liquid inlet channels 20 can extend between the tissue chamber 18 and a liquid inlet 28 or port. In some instances, an interior surface of a liquid inlet channel 20 can be textured to induce local turbulence in a liquid flowing therethrough to improve penetration of a labeling agent (or agents) into a tissue sample (see, e.g., Stott S L et al., *PNAS* 107:18392-18397, 2010). Although two liquid inlet channels 20 are shown in FIG. 1A, it will be appreciated that a fewer or greater number of liquid inlet channels can be included. In one example, the length of each liquid inlet channel 20 can be between about 1-15 mm, for example, about 6-9 mm (e.g., 7.5 mm).

Two liquid outlet channels 22 can extend between the tissue chamber 18 and a liquid outlet 30 or port. Although two liquid outlet channels 22 are shown, it will be appreciated that a fewer or greater number of liquid outlet channels 22 can be included. In one example, the length of each liquid outlet channel 22 can be between about 1-15 mm, for example, about 6-9 mm (e.g., 7.5 mm). In some instances, the liquid inlet channels 20 and the liquid outlet channels 22 can be spaced apart from each other by a distance D of about 1-4 mm (e.g., 2 mm). In other instances, the length of each liquid inlet channel 20 can be the same as, or different than, the length of each liquid outlet channel 22.

The microfluidic device 10 can include any number and configuration of fiducial markers 32 to assist in orienting the device and facilitating repetitive measurements. As shown in FIG. 1A, a plurality of fiducial markers 32 can be placed in a semi-circular pattern about the liquid outlet 30 and the liquid inlet 28. It will be appreciated that one or more fiducial markers 32, arranged in any desired pattern, can be placed about other components of the microfluidic device 10, such as the tissue chamber 18. In one example, fiducial markers 32 (e.g., fluorescent beads 34) (FIG. 1B) can be embedded in one or more walls 24 comprising the tissue chamber 18.

Figure 2:
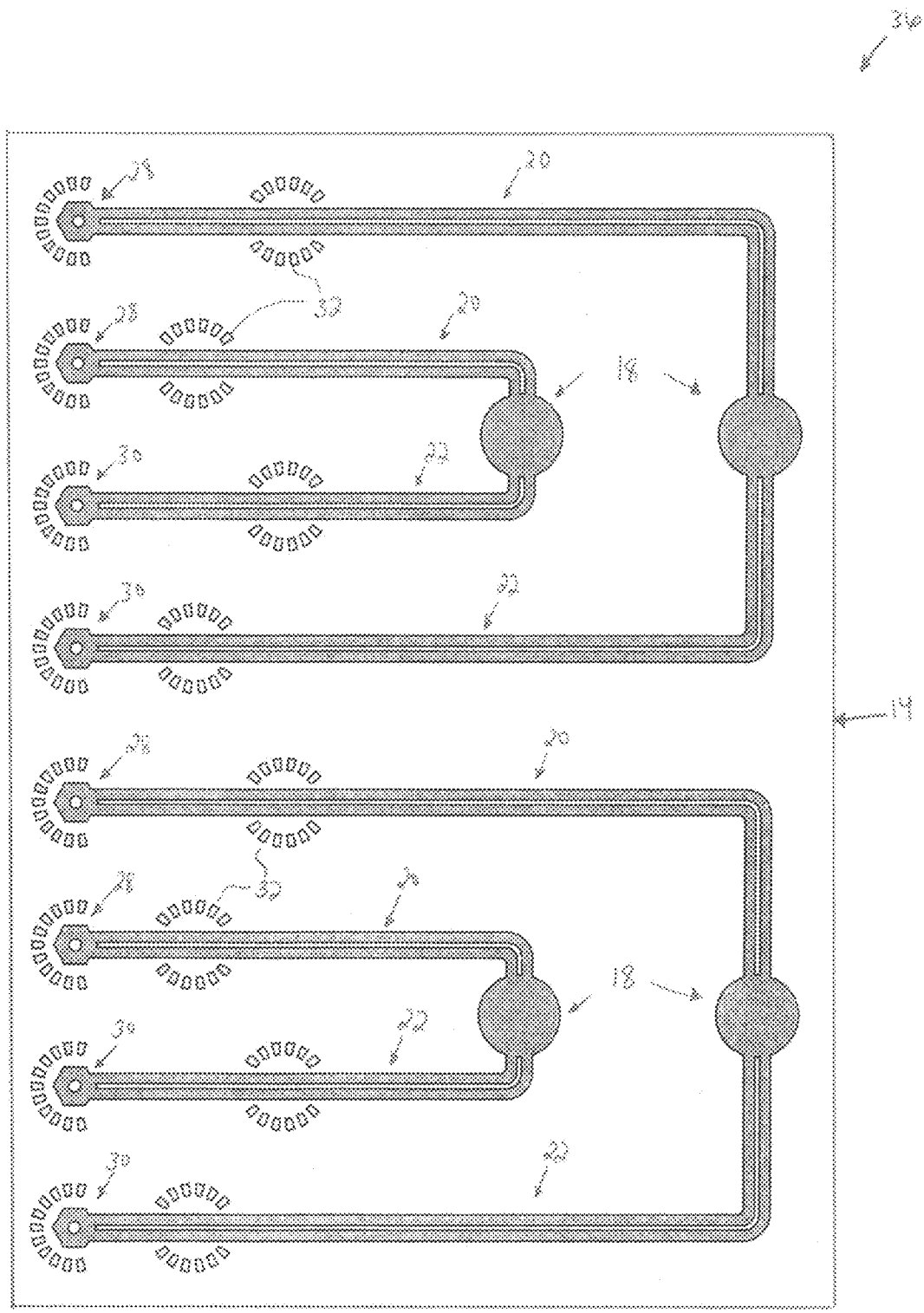
FIG. 2 is a plan view showing four microfluidic devices (FIG. 1A) arranged in a multiplex array.
Figure 4A:
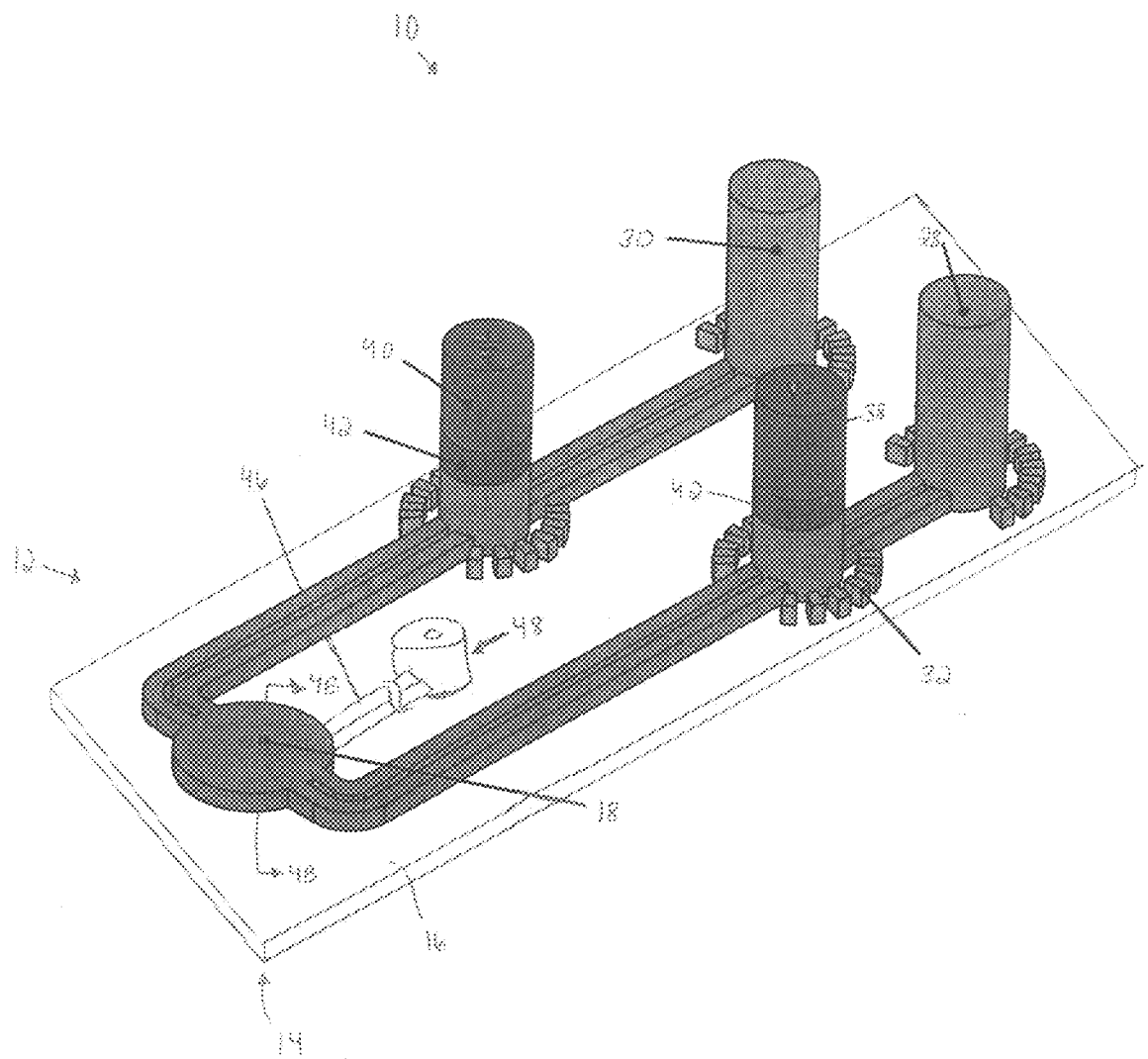
FIG. 4A is a perspective view of a microfluidic device for imaging a tissue sample constructed in accordance with yet another aspect of the present disclosure.
Figure 4B:
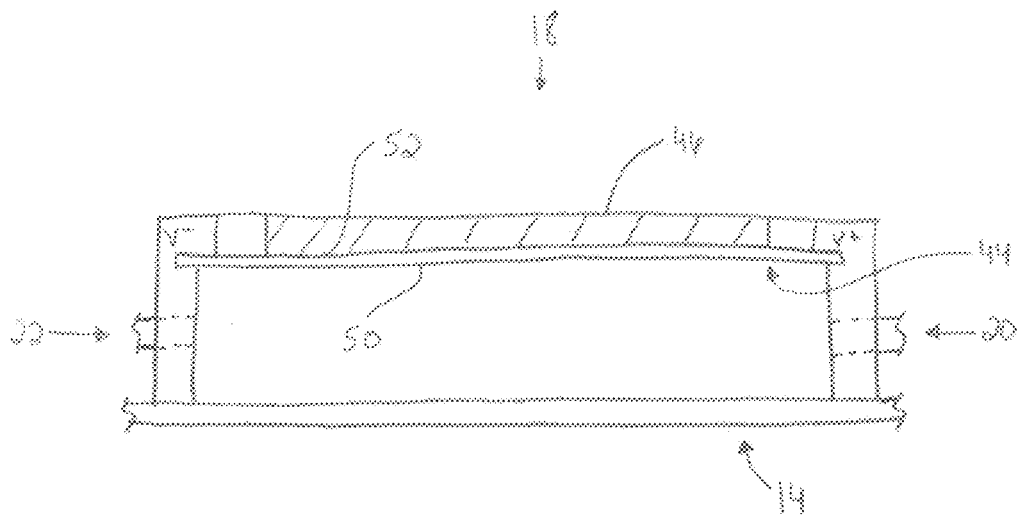
FIG. 4B is a cross-sectional view taken across Line 4B-4B in FIG. 4A.
Figure 4C:
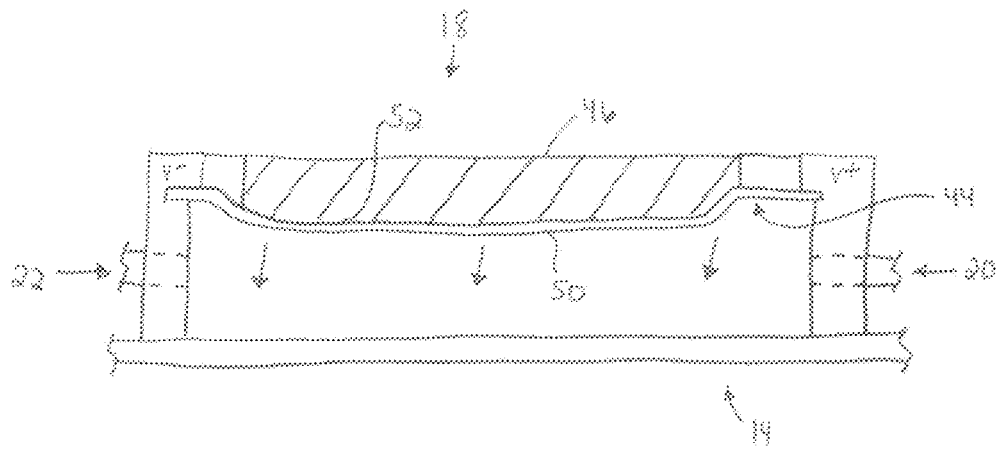
FIG. 4C is shows the application of pressure to a deformable membrane comprising the tissue chamber in FIG. 4B.
Figure 5:
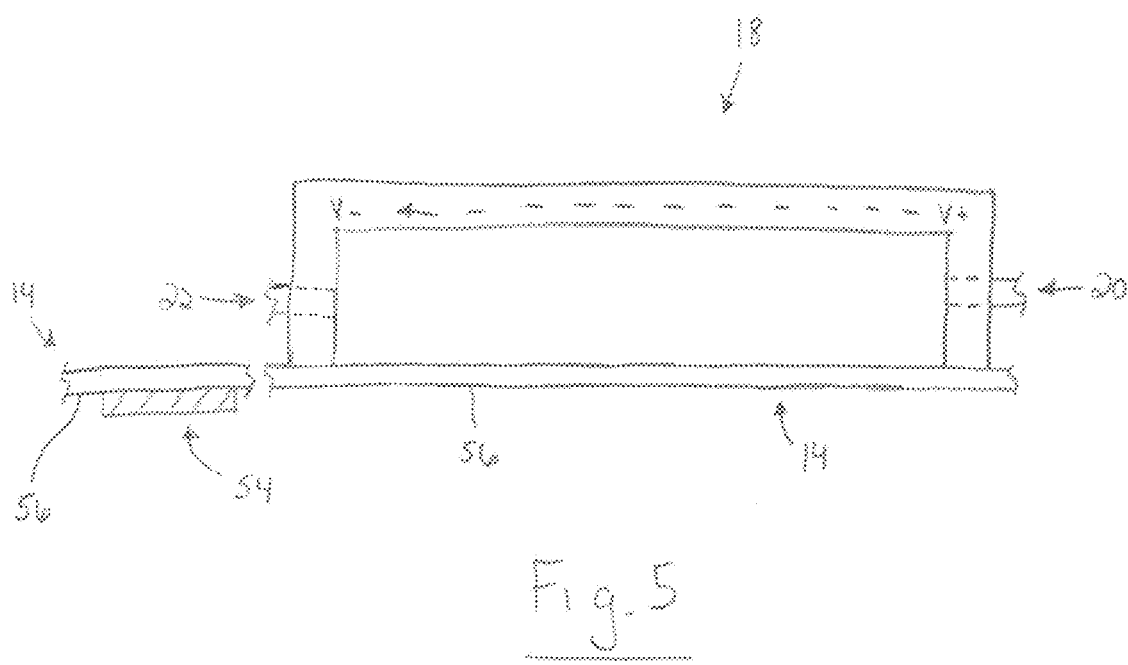
FIG. 5 is a cross-sectional view showing a piezoelectric element associated with a microfluidic device of the present disclosure.

The microfluidic device 10 can be constructed around a modular design to allow assembly into arrays for high-throughput applications. As shown in FIG. 2, for example, four microfluidic devices 10 can be formed as a single array 36 for multiplex analysis. In this case, the array 36 can include for separate tissue chambers 18, and their associated liquid inlet and outlet channels 20 and 22, all of which are disposed on a single transparent substrate 14 (e.g., a glass coverslip).

In another example, the microfluidic device 10 (FIG. 3) can additionally or optionally include first and second electrodes 38 and 40 that are disposed about the tissue chamber 18. The first and second electrodes 38 and 40 can be configured such that delivery of electrical energy thereto creates an electrical gradient across the tissue chamber 18. Advantageously, creation of the electrical gradient can drive an electrophoretic flow. The first and second electrodes 38 and 40 can be located atop respective plugs 42, which prevent escape of a liquid from the liquid inlet channels 20 and the liquid outlet channels 22 (respectively). In one example, a plug 42 can be made of agar. Therefore, in some instances, the first and second electrodes 38 and 40 are indirectly connected to the liquid inlet and liquid outlet channels 20 and 22. The first and second electrodes 38 and 40 can be spaced apart from one another, and from the tissue chamber 18, at a distance sufficient to create the electrical gradient. Although not shown, the first and second electrodes 38 and 40 can be in electrical communication with a power source for providing electrical energy thereto. As shown in FIG. 3, the structures comprising the first and second electrodes 38 and 40 can be at least partially surrounded by a plurality of fiducial markers 32.

In another example, the microfluidic device 10 (FIGS. 4A-B) can additionally or optionally include a deformable membrane 44, a pressure line 46, and a pressure port 48 adapted to receive positive or negative pressure. The deformable membrane 44 can be configured to selectively oscillate, upon application of pressure thereto (e.g., by means of an applied pressure signal), to induce a downward liquid flow (FIG. 4B) onto a tissue sample disposed in the tissue chamber 18. Advantageously, the downward liquid flow enhances penetration of a labeling agent (or agents) into the tissue sample. The deformable membrane 44 can be comprised of a flexibly resilient material (e.g., PDMS). The deformable membrane 44 can be disposed within the tissue chamber 18 such that a lower surface 50 of the membrane forms an upper surface that defines the interior of the tissue chamber. The pressure line 46 can be in fluid communication with an upper surface 52 of the membrane 44 to enable application of pressure to the upper surface. For example, the pressure line 46 can be located above the portion of the tissue chamber 18 comprising the membrane 44.

In another example, the microfluidic device 10 (FIG. 5) can additionally or optionally include one or more piezoelectric elements 54 that, upon delivery of an oscillatory voltage thereto, induces a vibration that propagates through the substrate 14 and the tissue chamber 18 into the tissue sample. Advantageously, this facilitates penetration (e.g., by increasing effective diffusion) of a labeling agent (or agents) into a tissue sample located in the tissue chamber 18. One example of a piezoelectric element 54 is described by Yazdi, S. et al., *Biomicrofluidics* 6, 044114 ((2012). In some instances, a piezoelectric element 54 can be connected to a second major surface 56 of the substrate 14 by glue. In other instances, a piezoelectric element 54 can be connected to the second major surface 56 of the substrate 14 by a non-adhesive gel so that the piezoelectric element is reusable. The piezoelectric element 54 can be located about the substrate 14 so that it does not interfere with imaging of the tissue sample. For example, the piezoelectric element 54 is not connected to the portion of the substrate 14 that is directly adjacent the tissue chamber 18 where the passage of light is required to obtain image data.

In another example, the microfluidic device 10 can additionally or optionally include one or more microwaves (not shown) coupled or connected thereto. One example of a microwave that can be connected to the microfluidic device 10 is described by Issadore, D. et al., *Lab. Chip* 9, 1701 (2009). Such a microwave can be operated to drive a labeling agent (e.g., polar antibodies) deep into the tissue sample during operation of the microfluidic device 10.

It will be appreciated that any of the components and features discussed above can be combined or omitted to form a microfluidic device 10, or array 36, of the present disclosure. One skilled in the art can determine such combinations based, for example, upon the particular application of the microfluidic device 10 or array 36.

Systems

Another aspect of the present disclosure can include a system 58 (FIG. 6) for imaging a tissue sample. The system 58 can comprise one or more microfluidic devices 10, a liquid source 60, a central acquisition and control module 62, and an imaging modality 64. Each of the microfluidic devices 10 can at least comprise a tissue chamber 18, a liquid inlet channel 20, and a liquid outlet channel 22. The tissue chamber 18 can be defined by a plurality of walls 24, at least one of which is transparent. The tissue chamber 18 can be sized and dimensioned to completely immobilize the tissue sample during imaging thereof. The liquid inlet channel 20 and the liquid outlet channel 22 can each be in fluid communication with the tissue chamber 18. The microfluidic device 10 can be immobilized on a translational microscopy stage 66. The liquid source 60 can be in fluid communication with the liquid inlet channel 20. The central acquisition and control module 62 can be in electrical communication with the liquid source 60 and the translational microscopy stage 66. The imaging modality 64 can be in electrical communication with the central acquisition and control module 62.

In some instances, one or more of the microfluidic devices 10 comprising the system 58 can be constructed like the microfluidic device shown in FIG. 3. It will be appreciated, however, that the microfluidic device(s) 10 comprising the system 58 can have any of the other configurations described herein, as well as other combinations of components and features discussed herein but not specifically shown.

Figure 6:
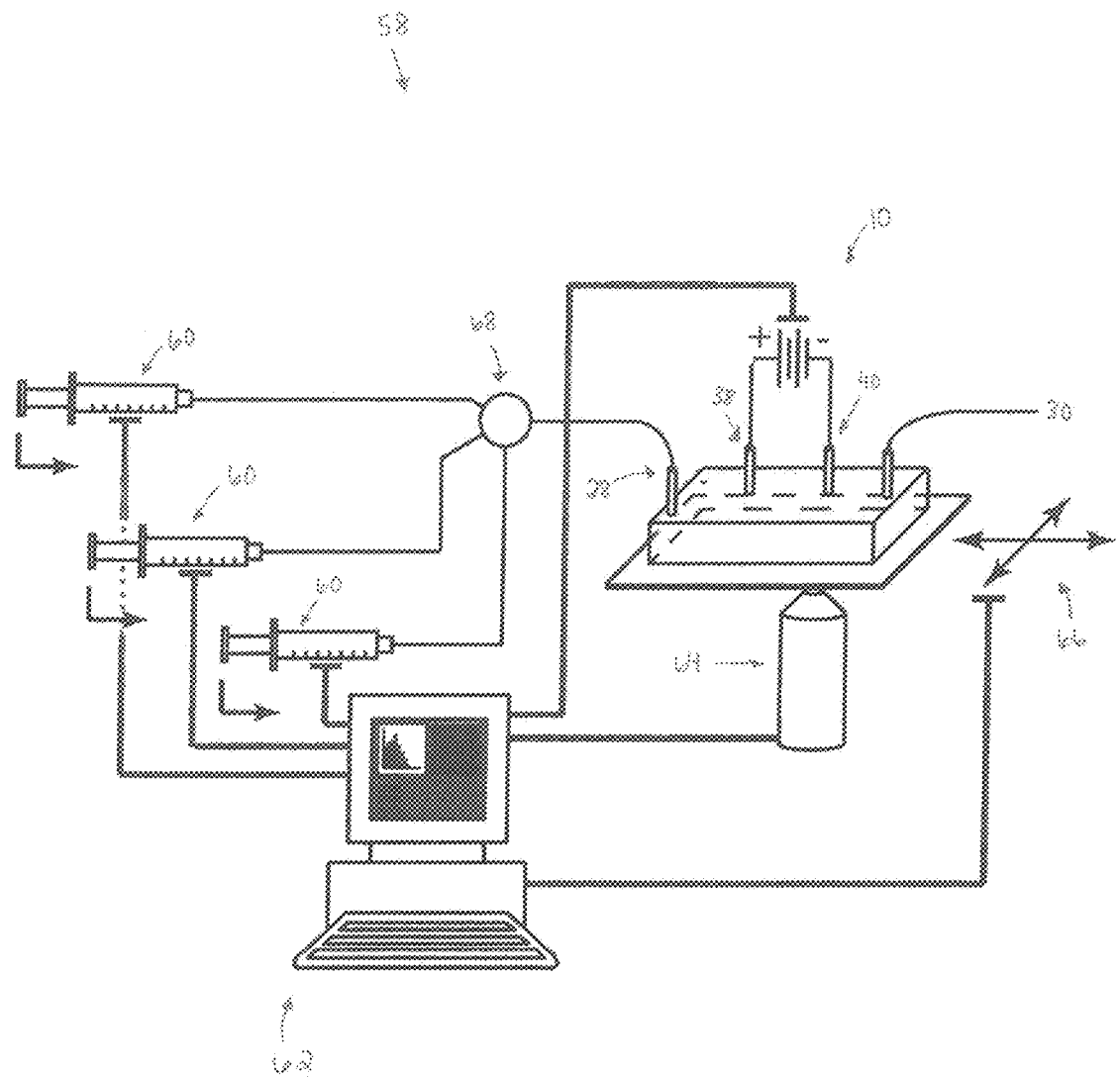
FIG. 6 is a schematic illustration of a system for imaging a tissue sample according to another aspect of the present disclosure.
Figure 7:
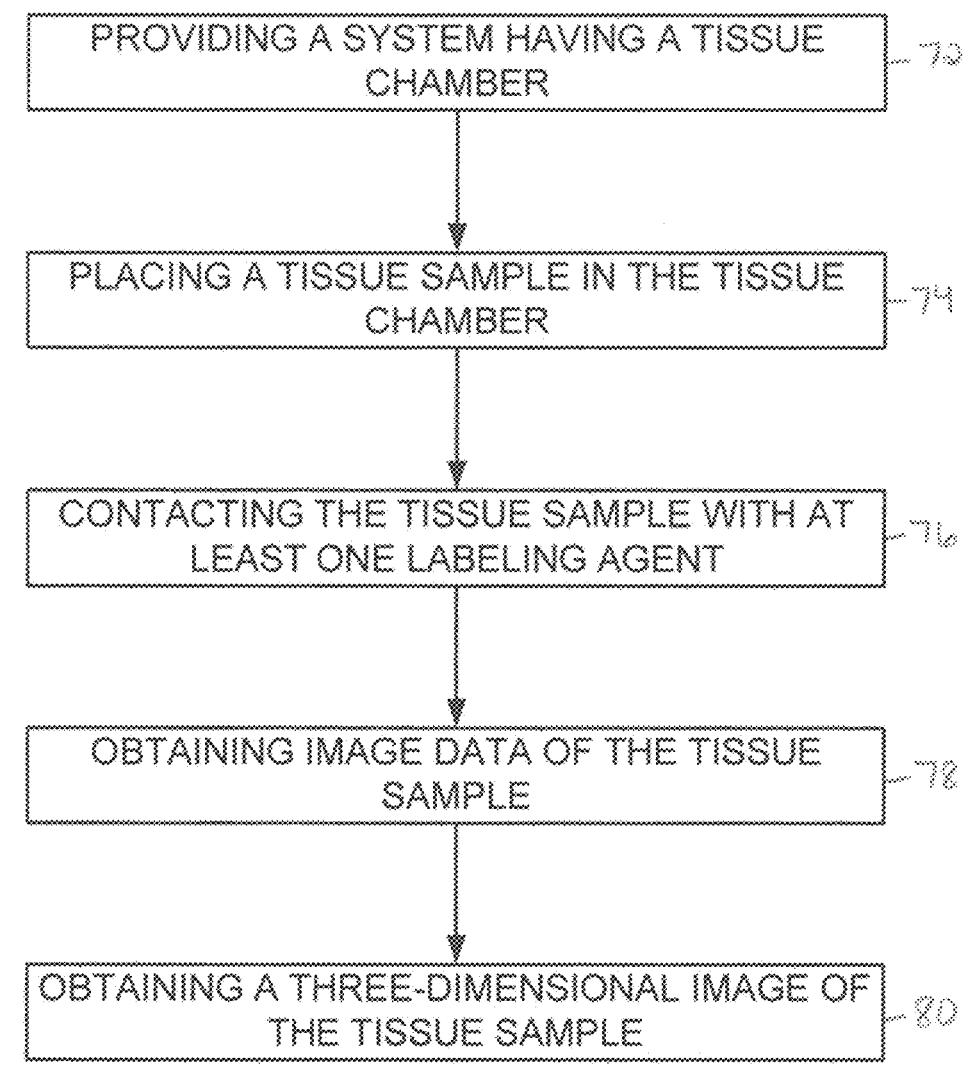
FIG. 7 is a process flow diagram illustrating a method for imaging a tissue sample according to another aspect of the present disclosure.

In some instances, the system 58 can include one or more liquid sources 60. As shown in FIG. 6, for example, the system 58 can include three liquid sources 60. The liquid source 60 can include any reservoir capable of holding a liquid (e.g., a reagent). Where the system 58 contains multiple liquid sources 60, the liquid contained in each of the liquid sources can be the same as or different than the liquid in the other liquid sources. In one example, the liquid source 60 can comprise a syringe. One or more of the liquid sources 60 can be in fluid communication with a pump 68 (e.g., a syringe pump, a peristaltic pump or a reciprocating pump), which may additionally or optionally be in electrical communication with the central acquisition and control module 62. In such instances, the pump 68 may also be connected to, and in fluid communication with, the liquid inlet 28 of the microfluidic device(s) 10.

In some instances, the central acquisition and control module 62 can include at least one computer and associated computational software programmed to operate components of the system 58. Non-limiting examples of computational software that can be included as part of the central acquisition and control module 62 can include software available from Imaris (BITPLANE AG, Zurich, Switzerland), Lab-VIEW (National Instruments, Austin, Tex.) and MetaMorph (Molecular Devices, Sunnyvale, Calif.). In some instances, the computer comprising the central acquisition and control module 62 can be interfaced with analog and digital output hardware (e.g., available from National Instruments) as well as hardware associated with the imaging modality 64. In one example, the central acquisition and control module 62 can be configured to track patient tissue samples such that the samples are not lost or mixed-up. This is highly advantageous given that the present disclosure can generate very large data sets (e.g., Terabytes per tissues sample). To this end, the software associated with the central acquisition and control module 62 can be programmed to include a database management function that contains information associated with generated image data, such as tissue sample processing conditions, antibody labels, other tissue sample information, etc.

The central acquisition and control module 62 can be in electrical communication with all or only a portion of the components comprising the system 58. In some instances, the central acquisition and control module 62 can be in wired or wireless communication with all or only a portion of the components comprising the system 58. The central acquisition and control module 62 can be configured to automate the tissue processing sequence and simultaneous imaging of multiple labeling agents using a preprogrammed experimental protocol. In this manner, the imaging sequences can be scheduled and conducted over relatively short periods of time to enable faster data collection and analysis. Further, as described below, the system 58 advantageously overcomes the challenges associated with imaging large area samples and deep tissues.

In some instances, the imaging modality 64 can include a confocal microscope, non-limiting examples of which include a spinning disc confocal microscope, a two photon confocal microscope, and a light-sheet based microscope. In other instances, the imaging modality 64 can include any microscope that includes selective plane illumination microscopy (SPIM) technology and/or is configured to perform SPIM. In this instance, the tissue chamber 18 can have a cylindrical and rotatable configuration to enable 360-degree viewing of the tissue sample.

Methods

Another aspect of the present disclosure can include a method 70 (FIG. 6) for imaging a tissue sample. The method 70 can generally include the steps of: providing a system 58 including one or more microfluidic devices 10 at least having a tissue chamber 18, a liquid source 60, a central acquisition and control module 62, and an imaging modality 64 (Step 72); placing a previously withdrawn tissue sample in the tissue chamber so that the tissue sample is immobilized therein (Step 74); flowing a liquid that contains at least one labeling agent through the tissue chamber (Step 76); obtaining image data of the tissue sample (Step 78); and obtaining a three-dimensional (3D) image of the tissue sample based on the obtained image data (Step 80).

The system 58 provided at Step 72 can be identically or similarly constructed as the system shown in FIG. 6. One skilled in the art will appreciate that the configuration of the system 58 used in the method 70 can depend, for example, upon the particular application.

At Step 74, a previously withdrawn tissue sample can be placed in the tissue chamber 18. Prior to placing the tissue sample in the tissue chamber 18, the tissue chamber can be formed (manufactured) so that its dimensions closely or exactly correspond to the dimensions of the tissue sample. This ensures that the tissue sample will be immobilized in the tissue chamber 18 during the method 70. In one example, the tissue sample can include a partial or whole tissue biopsy having a thickness of about 100 microns to about 5 cm or more. The ability of the method 70 to construct a 3D image of a partial or whole tissue biopsy having such a thickness is highly advantageous over current tissue-sectioning protocols, which use thin tissue sections (e.g., about 5-10 microns thick) for immunostaining. Such conventional tissue-sectioning protocols cannot faithfully interrogate whole tissue biopsy cytotypes (e.g., cellular identity, quantity, and location of various cell types that comprise a tumor and its 3D microenvironment).

In some instances, the tissue sample can be optically cleared prior to placement into the tissue chamber 18. Optical clearing refers to the process of cleaning a tissue sample of lipids, which scatter light and prevent 3D imaging. Optical clearing of a tissue sample is needed to ensure that light has an unobstructed path to the inside of a tissue sample. One example of a method for optically clearing a tissue sample is disclosed in Chung et al., *Nature Methods* 10:508-513 (2013) (hereinafter, "the CLARITY protocol"). Alternatively or additionally, the tissue sample can be optically cleared after the tissue sample is placed in the tissue chamber 18 using, for example, the CLARITY protocol. In this case, the chemicals and liquids associated with the CLARITY protocol are perfused through the channels 20 and 22 and tissue chamber(s) 18 comprising the system 58. It will be appreciated that each tissue sample may have a slightly different tissue clearing protocol, and that there may be sequential tissue clearing steps necessary to achieve the maximal level of tissue clearing before the immunostaining procedure(s). To this end, other examples of clearing protocols that can be used as part of the method 70 can include the iDISCO protocol described by Renier, N. et al., *Cell* 159(4):896-910 (2014), the CUBIC protocol described by Tainaka, K. et al., *Cell* 159:911-924 (2014), as well as those described and evaluated by Vlieg, R C et al., "Evaluation different passive optical clearing protocols for two-photon deep tissue imaging in adult intact visceral and neuronal organs", *bioRxiv*, 018622, and Ke, M T et al., *Nature Neuroscience*, 16(8):1154-1161 (2013).

In one example, a tissue sample (e.g., partial or whole tissue biopsy) can be harvested from a subject. The tissue sample can then be subject to a clearing protocol as discussed above. The inventors of the present application have discovered that normal or healthy (non-tumor) tissue is easy to optically clear, whereas optically clearing tumor tissue is difficult due to its especially dense (heterogeneous) nature as compared to normal or healthy tissue. Based on this discovery, the tissue sample (e.g., partial or whole tissue biopsy) can be subjected to a clearing protocol prior to placement in the tissue chamber 18. Tissue clearing solutions can be custom adapted, for example, to preferentially clear lipids, ECM (e.g., collagen), pigments etc. The differential clearing of tissue samples can be correlated with cell density, local ECM, etc., which provides information regarding the local environment of cells and can become a basis of initial diagnosis, either within a microfluidic device 10 or outside of it. The tissue sample can then be evaluated for any portion(s) that is/are not optically clear. For example, regions of interest (e.g., uncleared regions of a large tissue biopsy indicating a tumor) can be excised and placed into a microfluidic device 10 for additional clearing with an agent that removes excess collagen and makes the tumor region clearer and more accessible to antibody penetration. Several optical methods can be used to assess the differential clearing of a tissue sample, which in itself provides diagnostic and material information. Advantageously, this approach can dramatically reduce the costs associated with imaging and improve the success rate of early tumor detection.

In other instances, where the tissue sample is paraffinized, the tissue sample can be deparaffinized either prior to or after placement in the tissue chamber 18. One example of a deparaffinization protocol is described by Kumada, T. et al., *Modern Pathology*, 17(9):1141-1149 (2004).

At Step 76, at least one labeling agent can be contacted with the tissue sample. The labeling agent can be present in the liquid source 60 as a reagent, for instance. The central acquisition and control module 62 can activate the liquid source 60 (e.g., according to a pre-programmed protocol) to release a desired amount of the liquid at a desired rate. As the liquid flows through the liquid inlet channel 20 into the tissue chamber 18, the labeling agent can contact the tissue sample. The labeling agent present in the liquid can bind to its target analyte (if present) in the tissue sample. If desired, the central acquisition and control module 62 can cause electrical energy to be sent to the first and second electrodes 38 and 40 of the microfluidic device 10, thereby applying a desired electrical gradient to the tissue sample to drive electrophoretic flows.

In one example, flow in the microfluidic device 10 can be patterned due to the low mixing of individual channels 20. With multiple inlet channels 20, different regions of the tissue sample can receive multiple mixtures of different labeling agents (e.g., fluorophore-labeled antibodies) (see, for example, Frampton, J P et al., *Biotechnology Journal*, 10(1):121-125 (2015)). This will allow the simultaneous staining of multiple antibodies in the same 3D tissue sample at the same time.

As the liquid is flowed through the tissue chamber 18, the imaging modality 64 can be operated (by the central acquisition and control module 62) to obtain image data of the tissue sample (Step 78). Generated image data can then be relayed to the central acquisition and control module 62, where it can be recorded and/or processed. Once the central acquisition and control module 62 has recorded and/or processed the image data, the computational software associated therewith can generate a 3D image of the tissue sample (e.g., by co-registering multiple imaging datasets) (Step 80).

Figure 8:
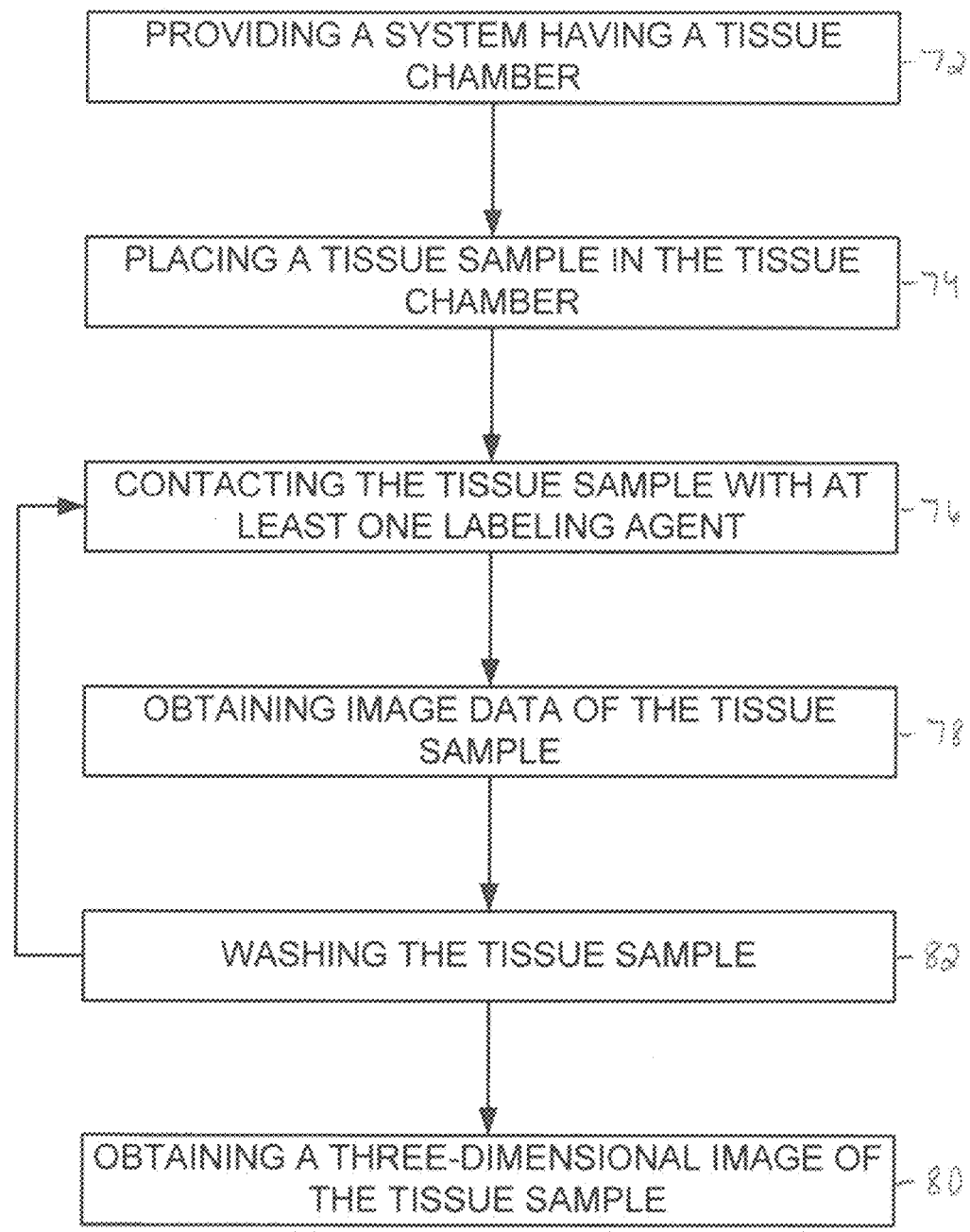
FIG. 8 is a process flow diagram illustrating another method for imaging a tissue sample according to another aspect of the present disclosure.

It will be appreciated the method 70 can be modified to permit multiple "on-chip" tissue clearing steps for repetitively imaging the same tissue sample with different labeling agents. At Step 82, the tissue sample can be optionally washed or treated, as shown in FIG. 8, to quench fluorophores after an image data set is obtained for a tissue sample (Step 78). Quenching "quenches" the fluorescent signal from a previous labeling agent. By quenching fluorescence of a labeled molecule, the same fluorescent channel (e.g., red, yellow or green) can be used to label another target analyte. One example of a quenching protocol is described by Gerdes, M J et al., *PNAS* 110(29):11982-11987 (2013). Once quenching has been completed, the tissue sample can again be contacted with the same or different labeling agent at Step 76. If desired, Steps 76, 78, and 82 can be repeated to obtain multiple image data sets of the tissue sample using the same or different labeling agent(s). The obtained multiple image data sets can then be processed (e.g., co-registered) to generate a 3D image of the tissue sample.

It will also be appreciated that one or all of Steps 76-82 can be performed automatically by the system 58. As discussed above, for example, this can be accomplished by programming the central acquisition and control module 62 with a particular imaging protocol and executing the program after the tissue sample has been placed in the tissue chamber 18.

Where the system 58 comprises multiple microfluidic devices 10 arranged in an array 36, multiple tissue samples (e.g., 10 or more) can be subjected to the method 70. The image data generated by such a multiplex approach can be co-registered and reconstructed into a single 3D image stack. Doing so is very challenging because labeling, imaging, quenching, labeling, imaging, and then successfully registering two images requires that these two images are on top of each other. This requires two things: (1) that the tissue sample is held relatively still; and (2) the presence of fiducial markers as landmarks for co-registration. Advantageously, both of these requirements are achieved by the present disclosure because: (1) the tissue chamber 18 is sized and dimensioned to immobilize tissue samples; and (2) labeling of the nuclei as the landmarks (e.g., using DAPI). Further, current tissue staining protocols enable researchers to label only up to three proteins of interest by utilizing three different fluorophore-labeled antibodies and imaging using multi-photon deep tissue imaging. The ability to multiplex multiple channels (e.g., labeled antibodies) simultaneously without the need to move the tissue samples provided by the method 70 advantageously provides increased data richness enabling a greater interface with systems-level investigation of spatial protein distributions in thick tissue samples.

After completing the method 70, the system 58 (e.g., the microfluidic device(s) 10) can be disassembled and the tissues sample(s) recovered for storage or further analysis.

As discussed above, the present disclosure can find application in a variety of research and clinical settings. In one example, the method 70 can find application in the early detection of breast cancer. A core needle breast tissue biopsy can be employed to obtain one or more tissue samples. Multiple, well-established breast cancer marker antibodies (e.g., HER2 and ER) and established TME markers (e.g., macrophage markers) can be imaged simultaneously after "on-chip" or "on-device" tissue sample clearing. Advantageously, the tissue samples can be directly imaged without disassembling the system 58 and, in particular, the microfluidic device(s) 10 thereof. By performing each process in situ without disturbing the tissue samples, each labeled constituent can be precisely registered in 3D space to provide an extremely rich 3D map of the TME. Thus, by using multiplexed immunofluorescence staining of the cleared tissue samples, multiple image stacks can be acquired to faithfully reconstruct the whole tissue samples in 3D, thereby allowing unprecedented and precise quantification of molecular changes in the TME.

The following example is for the purpose of illustration only and is not intended to limit the scope of the appended claims.

Example

Tissue samples were formalin-fixed and provided "as-is" (mouse mammary tissue) or custom-cut on a vibratome to a specified thickness (mouse brain tissue). Mammary samples were hand-cut with a razor blade to chamber-appropriate sizes (<2 mm in final length/width). Brain samples were biopsy-punched into 2 mm discs to match tissue chamber dimensions. Cut samples were stored in PBS until ready for loading (both mammary and brain).

The following steps were taken to load tissue samples: chips (feature side) and glass slides (transparent substrate) were cleaned with isopropyl alcohol and methanol, respectively, by spraying with solvent for approximately 30 seconds; chips (feature side) and slides were blown-dry with filtered, pressurized air and dried in an oven at 90° C. for 2 minutes; chips (feature-side) and slides were simultaneously treated with corona-discharge for 2 minutes; individual tissue samples were immediately transferred to chip chambers with forceps and the treated, feature-side contacted with treated side of glass coverslip; light pressure was applied by hand for 20 seconds; chips and tissue samples were baked in an oven at 90° C. for 15 minutes with a small weight applied from above to increase bonding; and tissue chambers were flooded with PBS for specimen storage until stain trial was run.

Next, breast cancer mouse model mammary duct was injected with trypan blue dye and with MCF-10A.DCIS tumor cell line. Tissue was then dissected, fixed, and loaded into the tissue chambers. The following staining procedure was then conducted: anti-Cytokeratin 8 Abcam (ab53280) was labeled with Zenon Alexa Fluor 647 rabbit IgG labeling reagent (Z-25360 Life Technologies, Carlsbad, Calif.) following manufacturer's instructions for a final dilution of 1:60 in PBS containing DAPI 1:1000 and 100 uM Phalloidin, Fluorescein isothiocyanate labeled (P5282 Sigma, St. Louis, Miss.); a total of 300 µL was prepared per chamber; tissue samples were stained at 5 µL/hour for 15.25 hours after tissue was cleared for 22.75 hours with CUBIC 1 at 5 µL/hour; and, after staining, the tissue was rinsed for one hour with PBS at 25 µL/hour and treated with CUBIC 2 for refractive index matching before imaging on the two-photon microscope. The results are shown in FIG. 9.

From the above description of the present disclosure, those skilled in the art will perceive improvements, changes and modifications. For example, although the term "microfluidic" is used herein, it will be understood that the dimensions of any device, structure, or component associated with the term will not be limited to the micro-scale. Rather, the term "microfluidic" can refer to devices, systems, and/or components of the present disclosure configured to handle small volumes of liquids or fluids and, moreover, that any device, structure, or component associated with the term can have dimensions greater or less than the micro-scale. Such improvements, changes, and modifications are within the skill of those in the art and are intended to be covered by the appended claims. All patents, patent applications, and publications cited herein are incorporated by reference in their entirety.

The following is claimed:

1. A microfluidic device for imaging a tissue sample, the device comprising:
   a tissue chamber defined by a plurality of walls, at least one of the plurality of walls being transparent;
   a deformable membrane disposed within the tissue chamber such that a lower surface of the deformable membrane and a surface of the at least one transparent wall define the tissue chamber, the deformable membrane being configured to oscillate, upon application of pressure thereto, to induce a downward liquid flow onto the tissue sample;
   at least one pressure line in fluid communication with the tissue chamber, the pressure line being in fluid communication with an upper surface of the deformable membrane to apply pressure to the upper surface of the deformable membrane;
   a liquid inlet channel that includes a liquid inlet and is in fluid communication with the tissue chamber; and
   a liquid outlet channel that includes a liquid outlet and is in fluid communication with the tissue chamber;

wherein the tissue chamber is sized and dimensioned to completely immobilize the tissue sample during imaging;

wherein the tissue chamber further includes:
- a first electrode that is connected to the liquid inlet channel and is spaced apart from the tissue chamber, the first electrode being located adjacent the liquid inlet; and
- a second electrode that is connected to the liquid outlet channel and is spaced apart from the tissue chamber and the first electrode, the second electrode being located adjacent the liquid outlet.

2. The device of claim 1, wherein an interior surface of the tissue chamber includes one or more grooves to permit liquid flow around the tissue sample.

3. The device of claim 1, wherein an interior surface of the liquid inlet channel is textured to induce local turbulence in a liquid flowing therethrough.

4. The device of claim 1, further comprising at least one piezoelectric element connected to an outer surface of the transparent wall such that delivery of an oscillatory voltage to the piezoelectric element induces a vibration that propagates through the transparent surface into the tissue sample.

5. The device of claim 1, further including a microwave connected thereto.

6. The device of claim 1, wherein the tissue sample is a whole tissue biopsy having a thickness of greater than 10 microns.

7. The device of claim 1, wherein the first and second electrodes are indirectly connected to the liquid inlet channel and the liquid outlet channel, respectively.

8. The device of claim 7, the first and second electrodes are located atop respective plugs, which prevent escape of a liquid from the liquid inlet channel and the liquid outlet channel, respectively.

9. The device of claim 1, wherein the tissue chamber includes a hydro-mold material disposed therein such that the hydro-mold material at least partially envelops the tissue sample to prevent the tissue sample from changing in orientation when liquid flows through the tissue chamber.

10. The device of claim 1, further including a transparent substrate, the transparent substrate having a first major surface;
wherein the tissue chamber, the liquid inlet channel, the liquid outlet channel, the first and second electrodes, and the pressure line are coupled to the first major surface of the transparent substrate; and
wherein the transparent wall of the tissue chamber comprises a portion of the first major surface of the transparent substrate.

11. The device of claim 1, wherein:
the first electrode is spaced apart from the liquid inlet; and
at least a portion of the liquid inlet channel is disposed between the first electrode and the liquid inlet;
wherein the portion of the liquid inlet channel disposed between the first electrode and the liquid inlet places the first electrode in fluid communication with the liquid inlet.

12. The device of claim 11, wherein:
the second electrode is spaced apart from the liquid outlet; and
at least a portion of the liquid outlet channel being disposed between the second electrode and the liquid outlet;
wherein the portion of the liquid outlet channel disposed between the second electrode and the liquid outlet places the second electrode in fluid communication with the liquid outlet.

13. A system for imaging a tissue sample, the system comprising:
one or more microfluidic devices, each of which includes:
- a tissue chamber defined by a plurality of walls, at least one of the plurality of walls being transparent, the tissue chamber being sized and dimensioned to completely immobilize the tissue sample during imaging thereof;
- a liquid inlet channel that includes a liquid inlet and is in fluid communication with the tissue chamber; and
- a liquid outlet channel that includes a liquid outlet and is in fluid communication with the tissue chamber;
wherein the microfluidic device is immobilized on a translational microscopy stage;
a liquid source in fluid communication with the liquid inlet channel;
a central acquisition and control module that is in electrical communication with the liquid source and the translational microscopy stage;
an imaging modality in electrical communication with the central acquisition and control module; and
wherein the tissue chamber further includes:
- a first electrode that is connected to the liquid inlet channel and is spaced apart from the tissue chamber, the first electrode being located adjacent the liquid inlet;
- a second electrode that is connected to the liquid outlet channel and is spaced apart from the tissue chamber and the first electrode, the second electrode being located adjacent the liquid outlet;
- a deformable membrane disposed within the tissue chamber such that a lower surface of the deformable membrane and a surface of the at least one transparent wall define the tissue chamber, the deformable membrane being configured to oscillate, upon application of pressure thereto, to induce a downward liquid flow onto the tissue sample; and
- at least one pressure line in fluid communication with the tissue chamber, the pressure line being in fluid communication with an upper surface of the deformable membrane to apply pressure to the upper surface of the deformable membrane.

14. The system of claim 13, further including:
a pressure source that is in fluid communication with the at least one pressure line and in electrical communication with the central acquisition and control module.

15. The system of claim 13, wherein an interior surface of the tissue chamber includes one or more grooves to permit liquid flow around the tissue sample.

16. The system of claim 13, wherein an interior surface of the liquid inlet channel is textured to induce local turbulence in a liquid flowing therethrough.

17. The system of claim 13, further comprising at least one piezoelectric element connected to an outer surface of the transparent wall such that delivery of an oscillatory voltage to the piezoelectric element induces a vibration that propagates through the transparent surface into the tissue sample.

18. The system of claim 13, further including at least one microwave connected to at least one of the microfluidic devices.

19. A microfluidic device for imaging a tissue sample, the device comprising:

a tissue chamber defined by a plurality of walls, at least one of the plurality of walls being transparent;

a liquid inlet channel that includes a liquid inlet and is in fluid communication with the tissue chamber;

a liquid outlet channel that includes a liquid outlet and is in fluid communication with the tissue chamber; and a deformable membrane disposed within the tissue chamber such that a lower surface of the deformable membrane and a surface of the at least one transparent wall define the tissue chamber, the deformable membrane being configured to oscillate, upon application of pressure thereto, to induce a downward liquid flow onto the tissue sample; and at least one pressure line in fluid communication with the tissue chamber, the pressure line being in fluid communication with an upper surface of the deformable membrane to apply pressure to the upper surface of the deformable membrane;

wherein the tissue chamber is sized and dimensioned to completely immobilize the tissue sample during imaging;

wherein the tissue chamber further includes:
  a first electrode that is connected to the liquid inlet channel and is spaced apart from the tissue chamber, the first electrode being located adjacent the liquid inlet; and
  a second electrode that is connected to the liquid outlet channel and is spaced apart from the tissue chamber and the first electrode, the second electrode being located adjacent the liquid outlet.

* * * * *